(12) United States Patent
Corby, Jr. et al.

(10) Patent No.: US 6,442,237 B1
(45) Date of Patent: Aug. 27, 2002

(54) REDUCED ACCESS X-RAY IMAGING DEVICE

(75) Inventors: Nelson Raymond Corby, Jr., Scotia; Clifford Bueno, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/682,615

(22) Filed: Sep. 27, 2001

(51) Int. Cl.[7] .............................................. G01B 15/06
(52) U.S. Cl. ........................................ 378/98.3; 378/58
(58) Field of Search ...................... 356/241.1; 250/368; 378/98.3, 51, 58, 59, 60, 63, 62, 98.8

(56) References Cited

U.S. PATENT DOCUMENTS

| | | | |
|---|---|---|---|
| 3,622,785 A | * 11/1971 | Irwin et al. | ............ 250/214 VT |
| 3,909,139 A | * 9/1975 | Wood | ...................... 356/241.1 |
| 4,253,447 A | 3/1981 | Moore et al. | |
| 4,261,344 A | 4/1981 | Moore et al. | |
| 4,491,865 A | 1/1985 | Danna et al. | |
| 4,561,776 A | * 12/1985 | Pryor | ...................... 356/241.1 |
| 4,963,018 A | * 10/1990 | West | ........................ 250/236 |
| 5,108,959 A | 4/1992 | Buchanan et al. | |
| 5,120,970 A | 6/1992 | Buchanan et al. | |
| 5,122,671 A | 6/1992 | Buchanan et al. | |
| 5,373,317 A | 12/1994 | Salvati et al. | |
| 5,391,320 A | 2/1995 | Buchanan et al. | |
| 5,594,253 A | 1/1997 | Bueno et al. | |
| 5,636,299 A | 6/1997 | Bueno et al. | |
| 5,784,434 A | * 7/1998 | Shieh | ......................... 378/191 |

* cited by examiner

Primary Examiner—David P. Porta
(74) Attorney, Agent, or Firm—Penny Clarke; Donald S. Ingraham (57) ABSTRACT

An x-ray imaging device includes a borescope and an x-ray detector positioned at a distal end of the borescope. The x-ray detector can be configured to be movable into and out of an optical path and can include a scintillation screen. The movably configured x-ray detector can be moved into the optical path, when x-rays are impinging, and out of the optical path, when a visible image of a test object is desired, facilitating navigation of the x-ray detector through a test object. The x-ray imaging device can include an imager, for converting an image to an electronic format. The imager can be positioned at the proximal end of the borescope, with the borescope including a waveguide, for guiding light to a proximal end thereof. Alternatively, the imager can be positioned between the distal end of the borescope and the x-ray detector.

45 Claims, 4 Drawing Sheets

REDUCED ACCESS X-RAY IMAGING DEVICE

BACKGROUND OF INVENTION

FIELD OF THE INVENTION

The invention relates generally to x-ray imaging and, more particularly, to reduced access x-ray imaging.

The early detection of corrosion and cracks is particularly important in the airline industry in order to remove and repair unsatisfactory or damaged components to prevent potentially harmful part failure. Because flaws often develop below the surface and spread to the surface of a component, detection of sub-surface flaws such as cracks and corrosion is necessary for early identification of an unsatisfactory airplane component, such as a wing or fuselage . Flaws also arise in hidden areas and in areas that are difficult to access on an aircraft, and these flaws must also be detected.

X-ray imaging provides a useful tool for detecting both sub-surface flaws and flaws that are hidden beneath other structure. X-ray imaging is well known and will not be described in detail. Briefly, a test object is exposed to a beam of x-ray radiation. The x-ray radiation is modulated by passage through the test object because x-ray absorption rates for cracks and other flaws differ from that of undamaged portions of the test object. The resulting x-ray flux is detected by an x-ray detector, which converts the flux information to electrical signals. The electrical signals are then processed for analysis or display.

Currently, x-ray imaging is used to inspect airplane components repeatedly throughout a component's life-span. Essentially, a plane is periodically taken out of service, its interior is removed, and the critical components, such as the wings, are disassembled. A target component, e.g. a wing or a horizontal stablizer, is then imaged, for example by covering the wing or horizontal stabilizer with an x-ray sensitive material and placing a powerful x-ray source within the wing. Although this x-ray inspection technique provides useful images of the airplane components, it has a number of drawbacks, including the large amount of time required to disassemble and reassemble an airplane and the associated cost. In addition, the disassembly and the reattachment of the wings and the fuselage introduce additional inspection steps. Namely, the interface between a reassembled wing and fuselage must be inspected. For example, the rivets must be probed. The additional inspection steps further increase the inspection cost and time.

Accordingly, it would be desirable to develop an x-ray imaging apparatus for inspecting remote portions of a test object, such as an airplane component. Additionally, it would be desirable if the apparatus could be manipulated and controlled from a position remote to the portion of the test object under examination. Similarly, it would be desirable for the apparatus to permit collection of x-ray image data at the remote position. Furthermore, it would be desirable if the apparatus could be maneuvered through narrow areas for inspecting reduced access portions of a test object to obviate disassembly of the test object. Such an apparatus would reduce inspection time and cost and, in addition, would eliminate the additional problems currently introduced by disassembling and reattaching components, such as airplane wings and fuselage.

SUMMARY OF INVENTION

Briefly, in accordance with one embodiment of the present invention, an x-ray imaging device includes a borescope and an x-ray detector positioned at a distal end of the borescope. Advantageously, the x-ray imaging device can be used to image remote portions of a test object.

BRIEF DESCRIPTION OF DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
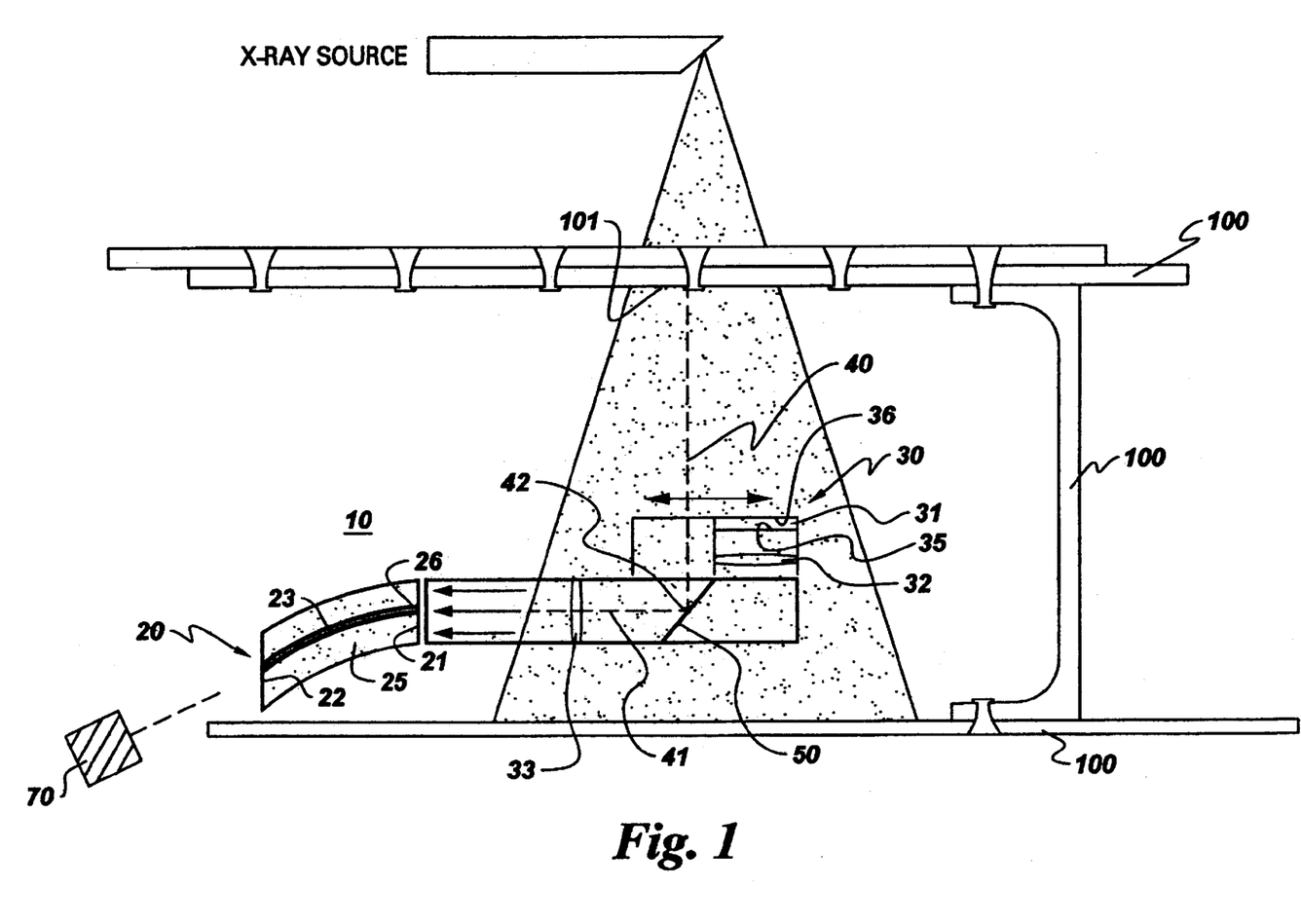
FIG. 1 shows an x-ray imaging device according to a first embodiment of the invention.

According to a first embodiment of the invention, an x-ray imaging device 10 includes a borescope 20 and an x-ray detector 30 positioned at a distal end 21 of the borescope, as shown in FIG. 1. Borescopes are standard devices and will not be described in great detail here. Briefly, borescopes are conventionally used to relay a visible image of a small area of a surface, which is located at some distance from an observer, to the observer. In order to inspect a remote component with reduced access, the borescope 20 is typically a long, flexible device. Typically, the borescope is tubular and ranges from about 0.2 m to about 10 m in length, depending on the desired application. However, the desired borescope length depends on the application, and the borescopes used in the present invention are not limited to a length range. A variety of borescopes are commercially available, for example from OLYMPUS Industrial and Everest VIT.

Advantageously, borescopes are controllable for maneuvering the distal end 21 through a remote, reduced access area of a component. As known to those skilled in the art, a borescope typically includes a control section at a proximal end thereof for remote movement of a distal articulation section. A common articulation means includes two pairs of cables that extend through the borescope from the control section to the distal articulation section. One common configuration includes a rack and pinion mechanism in the control section, which is actuated by a pair of steering knobs to steer the distal end two perpendicular directions, for example left and right and up-and-down. Alternatively, levers or a keyboard control could be used for steering. Of course, this discussion of articulation means is presented by way of example only. The present invention is not limited to any specific borescope and can be implemented with a variety of borescopes with varied articulation means.

Although borescopes can vary significantly in design, certain elements are common to most borescopes and will be briefly described here. An exemplary borescope body 25 includes a multilayer central tube (not shown) received within a housing. The housing is preferably formed of protective material such as PVC or rubber. In addition, providing a wire mesh (not shown) that surrounds the housing improves the wear resistance of a PVC-clad borescope.

An exemplary central tube (not shown) includes a waveguide, for example optical fibers 23, for relaying an image from a distal end 21 to a proximal end 22. In addition, articulation cables (not shown), and wires (not shown) extend through the exemplary central tube. The exemplary central tube further includes lumens (not shown) to accommodate the articulation cables, wires, and optical fibers. In addition, light for illumination is conveyed from an external source via additional optical fibers (also indicated by collective reference number 23) extending through the exemplary central tube.

For the x-ray imaging device 10 according to the first embodiment of the invention, a diameter of the borescope body 25 is selected based on the application. For passage through narrow areas, the diameter of the borescope body should be small, for example in a range of about 4 mm to about 8 mm. For narrower areas, borescope body diameters in a range of about 2 mm to about 3 mm may be desirable. For more easily accessible components, larger diameter borescope bodies can be used, with diameters in a range, for example, of about 8 mm to about 25 mm. Although a smaller borescope body diameter is desirable for maneuverability, the diameter should not be too small to accommodate the various cables, wires, and optical fibers. Accordingly, the desired borescope diameter depends on the application, and the borescopes used in the present invention are not limited to a diameter range.

According to one aspect, the borescope 20 includes a waveguide (not generally shown) for guiding electromagnetic radiation from a distal end 21 to a proximal end 22 of the borescope. The waveguide can include a plurality of relay optics (not shown). Alternatively, the waveguide can include an optical fiber or an optical fiber bundle, which are indicated schematically in FIG. 1 by reference numeral 23. Preferably, the optical fiber bundle is a coherent fiber bundle, with matching spatial arrangements of the optical fibers at the distal and proximal ends 21, 22 of the borescope. According to a second aspect, the borescope further includes at least one illumination optical fiber (also indicated by collective reference number 23 in FIG. 6 for conveying light for illumination from the proximal end 22 of the borescope.

According to a third aspect, the x-ray detector 30 is configured to be movable, such that the x-ray detector can be moved into the optical path 40, when x-rays are impinging, and out of the optical path 40, when a visible image of a test object 100 is desired. According to a fourth aspect, the x-ray detector is configured to slide into and out of the optical path 40, as schematically indicated in FIG. 1. A variety of movable mountings (not shown) for the x-ray detector can be used. For example, the x-ray detector can be mounted on a slider (not shown) which is engaged by a channel member (not shown) for sliding along the channel member. The slider can be actuated mechanically, such as by a guide wire extending through the borescope body 25. Alternatively, an electromagnetic or pneumatic slider actuation means can be employed.

Advantageously, a moveable x-ray detector 30 can be positioned out of the optical path 40, providing an unobstructed optical path between the distal end 21 of the borescope and a passage wall (not shown). In this manner, visible images of the passage can be obtained for navigation of the passage by the x-ray imaging device 10. Once the imaging device is positioned near the test object 100 to be imaged, the movable x-ray detector can then be moved into the optical path 40 to obtain x-ray images of the test object. In this manner, x-ray images of the test object are obtained, which are in close alignment to the visual images already collected.

According to a fifth aspect, the x-ray imaging device further includes an optical path changer 50 for aligning an optical path 40 of the x-ray detector and an optical path 41 of the borescope, as illustrated in FIG. 1. The optical path changer can include a reflector for aligning the optical paths 40, 41, for example a mirror. Alternatively, the optical path changer can adjust the optical paths refractively, for example via a fiber optic bundle (not shown). According to a sixth aspect, the optical path changer includes a tapered fiber optic bundle (not shown) to provide magnification or reduction, in order to more closely match a received image to a cross-sectional area of an imager 60 (shown in FIG. 2) or to a cross-sectional area of the distal end of the borescope. According to a seventh aspect, the borescope and the x-ray detector are configured such that the optical paths 41, 40 substantially coincide. For this latter configuration (not shown), the optical path changer is not needed.

According to an eighth aspect, the x-ray detector 30 includes a scintillation screen 31. Exemplary scintillation screens include conventional scintillation crystals such as cesium iodide (CsI), either undoped or doped. Exemplary CsI doping includes thallium or sodium. Exemplary scintillation screens include a scintillator crystal (not shown), a plurality of scintillator crystals, or bulk materials. Other exemplary scintillation screens include a spatially collimating array of scintillator crystals, as in the detector of the GE Digital Mammographic detection system (Senographe 2000D),and a fiber optic scintillator. Of course, this discussion of scintillation screen materials is presented by way of example only. The present invention is not limited to specific scintillation screen materials.

According to a ninth aspect, the scintillation screen 31 is relatively small. Advantageously, a small scintillation screen facilitates navigation of the x-ray imaging device 10 through narrow passages. However, a small scintillation screen produces a small image area, thereby increasing the time required to image a large component, such as an airplane wing. According to one aspect, the scintillation screen has dimensions of about 5 mm by about 5 to about 30 mm by about 30 mm. An exemplary scintillation screen is about 1 cm by about 1 cm by about 1 mm.

According to a tenth aspect, the scintillation screen is opaque to visible light incident on an incident edge 36 of the scintillation screen. The scintillation screen can be rendered opaque to incident visible light, for example, by providing an opaque coating (not shown), which is opaque to visible light, on the incident edge of the scintillation screen. Exemplary opaque coating materials include a thin metal film, paint, or plastic.

According to an eleventh aspect, the x-ray imaging device 10 further includes an imager 70 at a proximal end 22 of the borescope 20, as indicated schematically in FIG. 1. The imager converts light from the borescope to an electronic signal. More precisely, the imager generates an electronic representation of the spatial intensity pattern of light emitted from the scintillation screen 31, when the x-ray detector 30 is positioned in the optical path 40, and of light reflected from a surface (for example a surface 101 of a test object 100), when the x-ray detector is positioned out of the optical path 40. The electronic signal can then be analyzed or displayed by a processor (not shown) such as a computer (not shown).

According to a twelfth aspect, the imager is a photosensor array, which is in optical contact with the scintillation screen 31, for example, a charge coupled device (CCD) sensor, or a two dimensional array of photodiodes. Exemplary optical contacts between the imager and the scintillation screen include air spacing between the imager and the scintillation screen (with a small spacing being preferred, for example as small as about 0 to about 0.05 cm) and an optically transparent interface that better matches the spatial size of the scintillation screen and the imager, one example of the latter being a cascaded series of optical elements (not shown) having graduated indices of refraction. The optical elements can be air spaced or bonded to one another.

Figure 2:
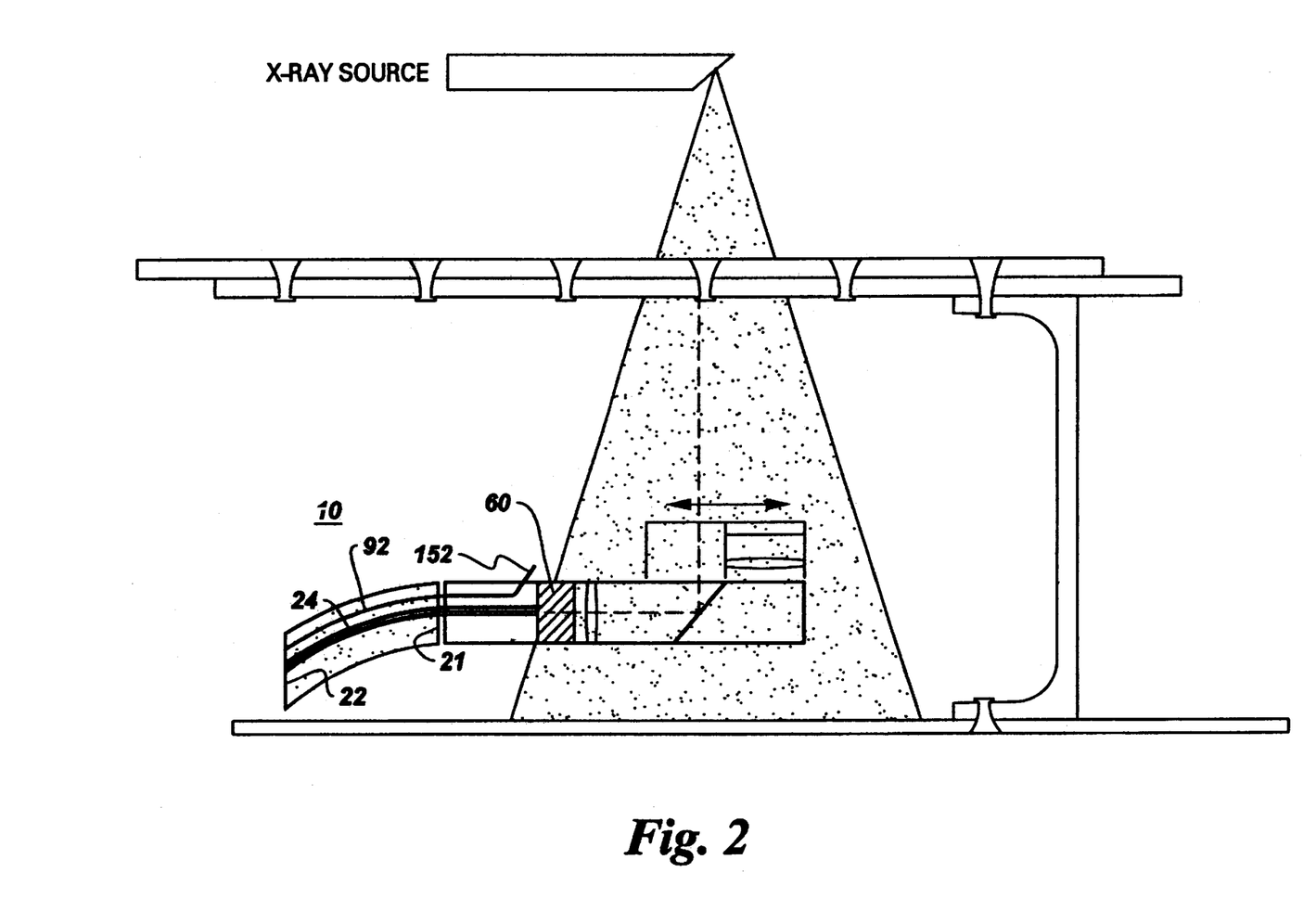
FIG. 2 shows an x-ray imaging device according to a second embodiment of the invention.

According to a thirteenth aspect, the x-ray imaging device 10 further includes an auxiliary optical system 32 positioned between the x-ray detector 30 and the distal end 21 of the borescope 20, as illustrated in FIG. 1. The auxiliary optical system can be used to move a focal plane (not shown) of a device, which is downstream from the x-ray detector, to an emission edge 35 of the x-ray detector. One example of a downstream device would be a CCD detector 60, as shown in FIG. 2. Another example of a downstream device is an edge 26 of a coherent fiber bundle 23, as shown schematically in FIG. 1. Preferably, the auxiliary optical system travels with the x-ray detector into and out of the optical path 40. An exemplary auxiliary optical system includes a lens, as illustrated in FIG. 1.

According to a fourteenth aspect, the x-ray imaging device 10 further includes a primary optical system 33. As shown in FIG. 1, the primary optical system is positioned between the x-ray detector 30 and the distal end 21 of the borescope 20. According to a fifteenth aspect, the primary optical system is positioned between the distal end of the borescope and an optical path changer 50. An exemplary primary optical system includes a lens, as illustrated in FIG. 1. The primary optical system is used to move the focal plane of the downstream device (e.g., the imager 60 shown in FIG. 2 or the edge 26 of the coherent fiber bundle 23) near a passage surface or a test object surface 101. In addition, the primary optical system is used in conjunction with the auxiliary optical system 32 to move the focal plane of the downstream device to the emission edge 35 of the x-ray detector 30.

A second embodiment of the invention is illustrated in FIG. 2. As FIGS. 1 and 2 indicate, the second embodiment is similar to the first embodiment in many respects. Accordingly, like parts are indicated by the same reference numerals, and only those aspects of the second embodiment, which differ from the first embodiment, are discussed. As illustrated in FIG. 2, the x-ray imaging device 10 according to the second embodiment includes an imager 60, which is positioned at the distal end 21 of the borescope 20 and which converts light to an electronic signal. More precisely, the imager generates an electronic representation of the spatial intensity pattern of light emitted from the scintillation screen 31, when the x-ray detector 30 is positioned in the optical path 40, and of light reflected from a surface, when the x-ray detector is positioned out of the optical path 40. According to one aspect, the imager is a photosensor array, which is optically coupled to the scintillation screen 31, for example, a charge coupled device (CCD) sensor, or a two dimensional array of photodiodes.

For the x-ray imaging device 10 according to the second embodiment, the borescope 20 relays the electronic signal from the imager to the proximal end 22 of the borescope. Accordingly, according to a second aspect, at least one wire 24 extends through the borescope as illustrated schematically in FIG. 2. For example, the wire can extend through a lumen (not shown) within the borescope. The electronic signal can then be analyzed or displayed by a processor (not shown) such as a computer (not shown). Because the visual and x-ray images are conveyed electronically through the borescope for the second embodiment, the borescope need not include a spatially coherent waveguide, such as a coherent fiber bundle. However, according to a second aspect, the borescope includes at least one illumination optical fiber 92 for illuminating a surface during visual imaging. As illustrated in FIG. 2, an exemplary illumination optical fiber includes a light source end 152, for illuminating the test object during visual imaging.

Figure 3:
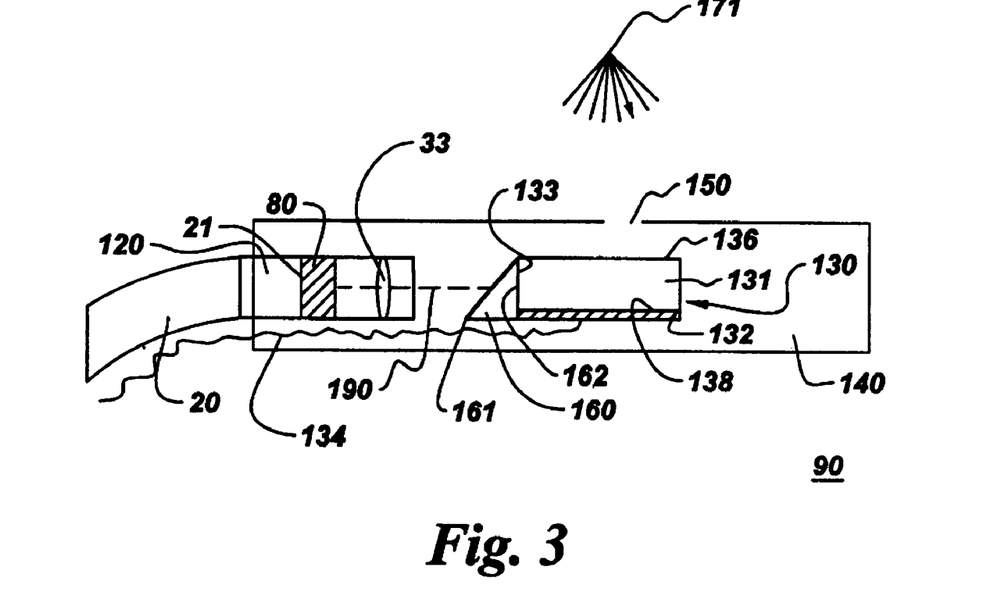
FIG. 3 shows an x-ray imaging device, according to a third embodiment of the invention, in an x-ray imaging position.
Figure 4:
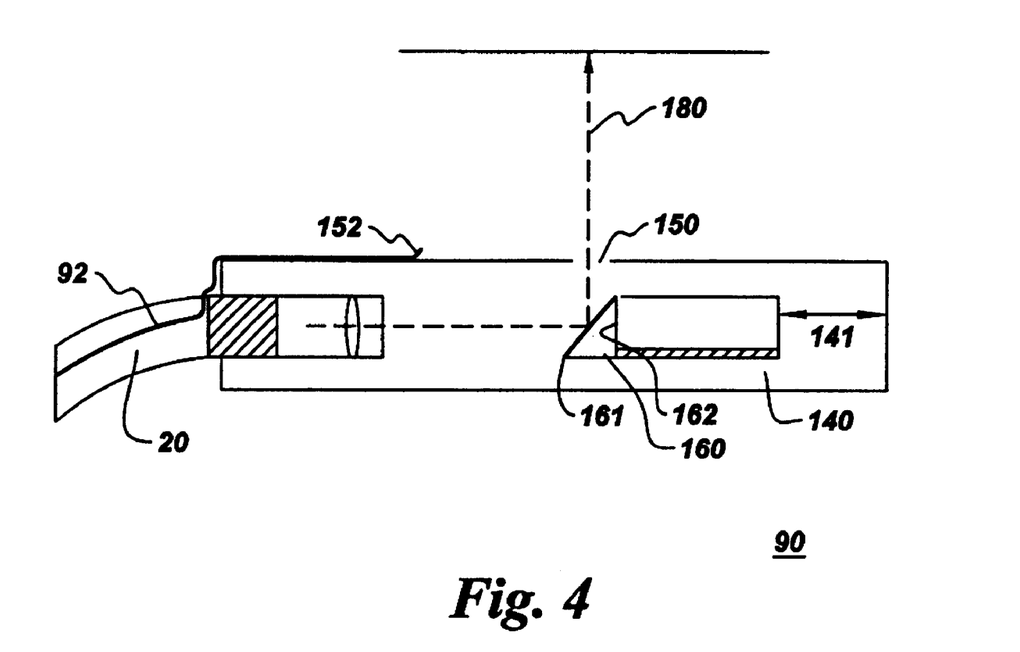
FIG. 4 shows the x-ray imaging device of FIG. 3, in a visual imaging position.

A third embodiment of the invention is illustrated in FIGS. 3 and 4, with like parts indicated by the same reference numerals used with respect to the first and second embodiments. An x-ray imaging device 90 according to the third embodiment includes a borescope 20 and a box 140 extending over an imaging end 120 of the borescope, as illustrated in FIG. 3. The box includes an aperture 150. According to one aspect, the box is attached to the borescope, for example by crimping or adhesive means, such as glue. According to a second aspect, the box is small, for example about 2 cm by about 4 cm by about 1 cm. Advantageously, a small box is more easily maneuvered through narrow passages.

According to a third aspect, the box 140 is substantially opaque to visible light, transmitting less than about 0.1% of visible light, but is substantially transparent to x-rays, having an x-ray absorptivity of about 0.1% or less. The box can be formed, for example, of plastic. Advantageously, such a box transmits visible light only through the aperture 150, whereas x-rays permeate the box such that an x-ray imager 130 having a surface area larger than the distal end of the borescope (approximately 2 cm by 2 cm) can be used.

The x-ray imaging device 90 further includes an x-ray imager 130 and an optical path changer 160, which are mounted in the box 140. According to a fourth aspect, the x-ray imager 130 and the optical path changer 160 are slidably mounted in the box 140, for sliding between a visual imaging position, as shown in FIG. 4, and an x-ray imaging position, which is shown in FIG. 3. Any of the movable mountings (not shown) discussed above with respect to the x-ray detector 30 for the first embodiment could be employed to slidably mount the x-ray imager and the optical path changer in the box. According to a fifth aspect, the x-ray imager and the optical path changer are constrained to slide together, along a sliding axis 141. According to a sixth aspect, the x-ray imager and optical path changer slide by about half the length of the x-ray imager, for example about 15 mm.

As indicated in FIG. 4 and according to the fourth aspect, the optical path changer 160 is aligned with the aperture 150 of the box 140, in the visual imaging position, allowing a visual image of a surface to be formed. In contrast, in the x-ray imaging position illustrated in FIG. 3, the x-ray imager is exposed to an x-ray source 171, for formation of an x-ray image of the test object (not shown). Advantageously, the optical path changer and x-ray imager can be positioned in the visual imaging position during navigation of the x-ray imaging device through a test object, such as an airplane wing. After the x-ray imaging device is maneuvered to a portion of the test object of interest, the x-ray imager and optical path changer can then be moved to the x-ray imaging position.

Alternatively, for applications not requiring alignment of visible and x-ray images, a shutter (not shown) is positioned on the aperture 150. According to this aspect, the shutter is opened for visible imaging and shut for x-ray imaging. For this aspect, the x-ray imager 130 and the optical path changer 160 are not slidably mounted in the box 140. However, as stated above the x-ray imaging device 90 of this aspect will not provide alignment of visible and x-ray images and thus may be unsatisfactory for applications requiring both visible and x-ray images of an identical portion of a test object.

According to a sixth aspect, the optical path changer 160 is mounted at a rear edge 133 of the x-ray imager 130, as illustrated in FIG. 3. By thus positioning the optical path changer between the x-ray imager and a distal end 21 of the borescope 20, the optical path changer blocks light incident on a rear face 162 of the optical path changer, in the x-ray imaging position, as indicated in FIG. 3. In this manner, the optical path changer reduces the background light incident on the distal end 21 of the borescope, thereby increasing the sharpness of an x-ray image of the test object (not shown).

According to a seventh aspect, the optical path changer 160 is a prism (also indicated in FIGS. 3 and 4 by reference numeral 160) with a reflective front face 161. As indicated in FIG. 4, the reflective front face reflects light toward the distal end 21 of the borescope 20. Preferably, the prism is a 45° prism, in order to reflect light incident on an optical axis 180 to an optical axis 190 of the borescope, where the optical axes 180, 190 are perpendicular. It is also possible to orient the test object 100 and borescope such that the optical. axes 180, 190 intersect at non-right angles (not shown). For the later configurations, the angle of the prism would be adjusted accordingly.

According to an eighth aspect, the optical path changer 160 is a mirror (not shown), which is oriented to reflect light from the aperture toward the distal end 21 of the borescope 20. An exemplary mirror is reflective on a front face 161 and absorptive on a rear face 162, so that the mirror reflects light toward the borescope during visual imaging and blocks light from the borescope during x-ray imaging.

According to a ninth aspect, the optical path changer 160 is spectrally sensitive, such as a dielectric mirror.

According to a tenth aspect, the x-ray imaging device 90 further includes a primary optical system 33. One exemplary primary optical system includes a lens, as illustrated in FIG. 3. The primary optical system is positioned between the distal end 21 of the borescope 20 and the optical path changer 160, as shown in FIG. 3. The primary optical system is used to move a focal plane of a downstream device (e.g., a CCD sensor, not shown) near a passage surface (not shown) or a test object surface (not shown).

X-ray imaging is performed using the x-ray imager 130, which includes an x-ray detector 131, as indicated schematically in FIG. 3. The x-ray detector converts x-rays incident on a front face 136 of the x-ray detector to photons, which are emitted from a rear face 138 thereof. According to an eleventh aspect, the x-ray detector 131 includes a scintillator. Exemplary scintillators are discussed above with respect to the first embodiment.

The x-ray imager 130 further includes an imager 132, and the x-ray imaging device 90 further includes a conductive path 134, which are indicated schematically in FIG. 3. The imager converts the photons, emitted from the rear face of the x-ray detector, to an electronic signal, which signal is relayed by the conductive path to a proximal end (not shown) of the borescope 20.

According to a twelfth aspect, the x-ray detector 131 is bonded to the imager 132. Preferably, the x-ray detector and imager are bonded such that their interface is optically transparent ("optically coupled"). Exemplary bonding means include the use of optically transparent glues or cements or of mechanical attachment means, such as clamping. Alternatively, the bonding can be provided by growing the x-ray detector on the imager, for example by growing a CsI scintillator on an amorphous Silicon ($\alpha$-Si) imager.

According to a thirteenth aspect, the imager 132 is a photosensor array, which is optically coupled to the x-ray detector 131. Exemplary imagers include a charge coupled device (CCD) sensor and a two dimensional array of photodiodes.

The conductive path 134 extends from the imager 132 to a proximal end (not shown) of the borescope 20, to relay the electronic signal. One exemplary conductive path includes one or more wires, schematically indicated by the same reference numeral 134 in FIG. 3. The wire extends from the imager and can either be integral to the imager or connected thereto. According to one aspect, the wire extends to the proximal end of the borescope along an exterior of the borescope, as illustrated in FIG. 3. Preferably, the wire extends through the borescope to the proximal end thereof. More preferably, the wire extends through a lumen (not shown) provided in the borescope. Equivalently, the conductive path can include one or more additional wires, which extend along an exterior of the borescope or through the borescope to the proximal end thereof. The additional wire can be connected to the wire either inside or outside the borescope.

Although the borescope 20 has been discussed in some detail with respect to the first embodiment, a few aspects thereof bear repeating. An exemplary borescope includes illumination optical fibers 92 for conveying light from an external source (not shown) at the proximal end (not shown) of the borescope, as illustrated schematically in FIG. 4. The exemplary borescope further includes a lumen (also indicated by reference numeral 92) through which the illumination optical fibers extend. As indicated in FIG. 4, an exemplary optical fiber extends around the box 140 and includes a light source end 152 for illuminating a test object. The exemplary borescope further includes signal wires (not shown), for example for energizing the imager 132, and a lumen (not shown) though which the signal wires extend. The signal wires also extend around the visible imager 80 for connection to the imager 132. Moreover, the exemplary borescope includes articulation means (not shown) and a control section for remote movement of the distal end.

According to a fourteenth aspect, the x-ray imaging device 90 further includes a visible imager 80. The visible imager converts an image received from the optical path changer 160 to an electronic signal. The electronic signal can then be relayed, analyzed, or displayed. According to a fifteenth aspect, the visible imager is positioned at a proximal end (not shown) of the borescope. For this configuration, the borescope preferably includes a coherent waveguide (not shown) for conveying an image from the distal end 21 of the borescope to the visible imager. More preferably, the waveguide includes a coherent fiber optic bundle (not shown), as discussed above with respect to the first embodiment.

Alternatively, the visible imager 80 is positioned at the distal end 21 of the borescope 20, as illustrated in FIG. 3. For this configuration, the borescope need not include a coherent waveguide. Instead the borescope includes a conductive path (not shown), for example one or more wires (not shown), for relaying the electronic signal from the visible imager to the proximal end of the borescope for processing or display.

According to a sixteenth aspect, the visible imager 80 is a photosensor array, which is optically coupled to the x-ray detector 131. Exemplary imagers include a charge coupled device (CCD) sensor and a two dimensional array of photodiodes.

According to a seventeenth aspect, the x-ray imager 130 includes the x-ray detector 131, which in turn comprises a photoconductor, which is also indicated by reference numeral 131. The photoconductor converts the incident x-rays into excess electron-hole carriers in the photoconductor. Consequently, the photoconductor replaces the scintillation screen discussed above. Exemplary photoconductors include amorphous Selenium or Lead Iodide, with an exemplary minimum thickness of about 100$\mu$m to about one mm.

According to an eighteenth aspect, the x-ray imager 130 further includes a read-out structure, which is also indicated by reference numeral 132 in FIG. 3. Exemplary readout structures include thin-film-transistor read-out structures. The read-out structure converts the excess carriers generated in the photoconductor 131 to an electronic signal characterizing the x-ray image, which signal is relayed by a conductive path 134 to a proximal end (not shown) of the borescope 20.

Figure 5:
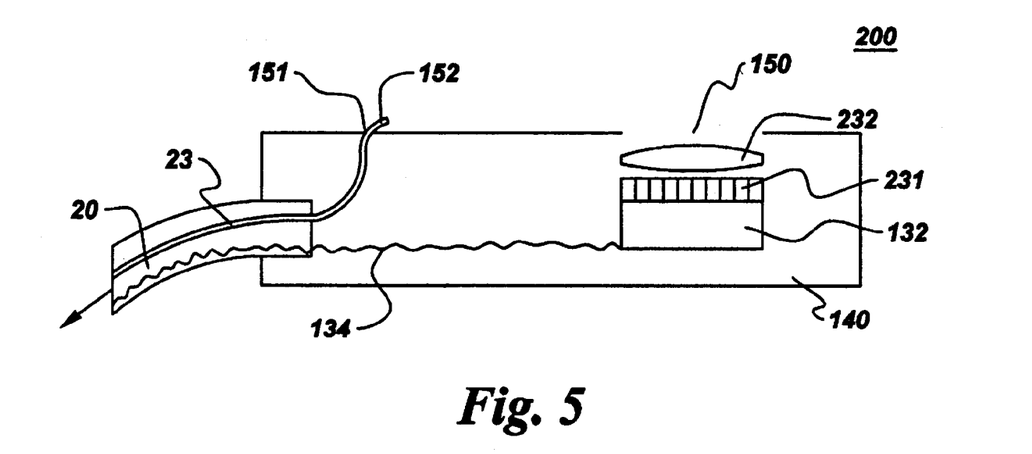
FIG. 5 shows an x-ray imaging device according to a fourth embodiment of the invention, in a visible imaging position.
Figure 6:
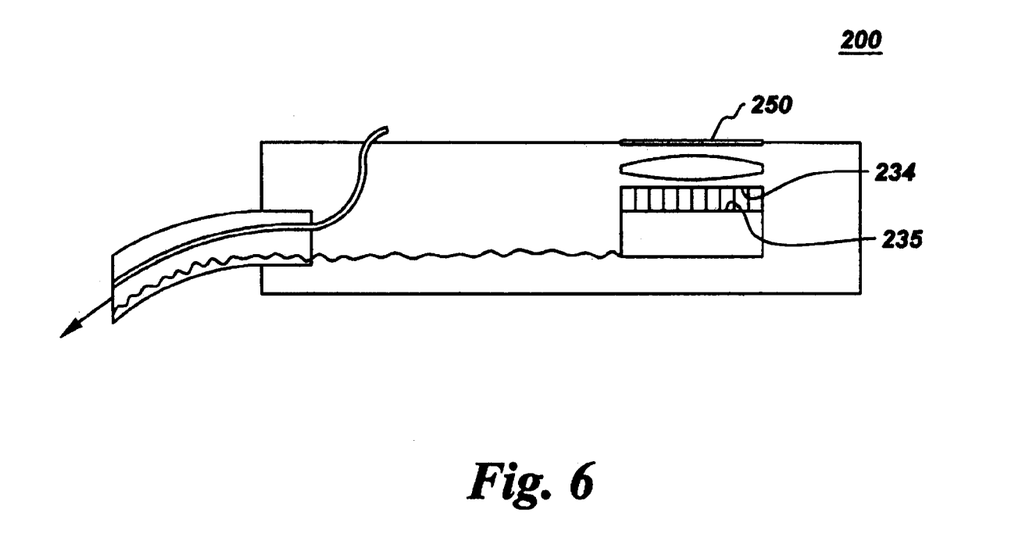
FIG. 6 shows the x-ray imaging device of FIG. 5, in an x-ray imaging position.

A fourth embodiment of the invention is illustrated in FIGS. 5 and 6, with like parts indicated by the same reference numerals used with respect to the first, second, and third embodiments. An x-ray imaging device 200 according to the fourth embodiment includes the borescope 20 and the box 140 extending over the imaging end 120 of the borescope, as illustrated in FIG. 5. The box includes the aperture 150. According to one aspect, the box is attached to the borescope, for example by crimping or adhesive means, such as glue.

According to a second aspect, the box 140 is substantially opaque to visible light, as discussed above with respect to the third embodiment. Advantageously, such a box transmits visible light only through the aperture 150, whereas x-rays permeate the box. According to a third aspect, the aperture 150 is fitted with a shutter 250, as illustrated in FIG. 5. Exemplary shutters include shutters used in 35 mm single lens reflex cameras. The shutter is open during visible imaging, as illustrated in FIG. 5 and is shut during x-ray imaging, as indicated in FIG. 6. According to this aspect, the borescope 20 includes means (not shown) to manipulate the shutter, for example electrical or mechanical means.

According to a fourth aspect, the shutter is "substantially opaque" to visible light, as this phrase is used above with respect to the third embodiment. According to this aspect, the shutter possesses an x-ray absorptivity less than about twenty percent. According to a fifth aspect, the shutter is "substantially transparent" to x-rays, as this phrase is used above with respect to the third embodiment.

The x-ray imaging device 200 further includes an x-ray detector 231 and an imager 132. Incident x-rays are converted by the x-ray detector to visible photons, which are converted by the imager to an electronic signal. The x-ray imaging device further includes a conductive path 134 for conveying the electronic signal to the proximal end (not shown) of the borescope. According to a sixth aspect, the x-ray detector and imager are attached to the borescope 20. According to a seventh aspect, the x-ray detector and imager are mounted to the box 140.

According to an eighth aspect, the aperture 150 and the x-ray detector 231 are coextensive, as shown in FIG. 5. According to this aspect, the shutter 250 possesses an x-ray absorptivity less than about twenty percent. According to a ninth aspect, the shutter is substantially transparent to x-rays.

According to a tenth aspect, both the shutter and the box possess an x-ray absorptivity less than about twenty percent. According to an eleventh aspect, the shutter and the box are substantially transparent to x-rays.

According to an eleventh aspect, the x-ray detector 231 is a fiber optic scintillator (also indicated by reference numeral 231). An exemplary fiber optic scintillator comprises a plurality (for example, more than a million) of luminescent fibers (not shown), each luminescent fiber being surrounded by a glass cladding (not shown) forming a cladded fiber (not shown). The cladded fibers are transparent to visible light and are formed into bundles. In this manner, the fiber optic scintillator provides a fiber optic imaging plate (also indicated by reference numeral 231) that acts as an image conduit when an optical image is focused onto an input surface 234 of the fiber optic scintillator. Moreover, because the fibers are luminescent, visible light is produced when ionizing radiation is absorbed in the fibers. In this manner, the fiber optic scintillator is configured to convey a converted image of an absorbed x-ray pattern to an output surface 235 of the fiber optic scintillator. Consequently, the fiber optic scintillator can be used both to transmit an optical image and to transmit a converted x-ray image to an image collection device, such as the imager 132.

Exemplary imagers include a photosensor array, which is in optical contact with the fiber optic scintillator, such as a charge coupled device (CCD) sensor or a two dimensional array of photodiodes. Exemplary optical contacts between the imager and the fiber optic scintillator include an optically transparent interface and an optically transparent interface that better matches the index of refraction of the two media, as discussed above with respect to the first Embodiment.

According to a twelfth aspect, the x-ray imaging device 200 further includes an optical system 232, such as a lens (also indicated by reference number 232). The optical system is configured to focus visible light onto the input surface 234 of the fiber optic scintillator 231. Exemplary lenses are formed of optically transparent materials and possess a low x-ray absorptivity, for example an x-ray absorptivity less than about ten percent to about twenty percent. Any x-ray shadow pattern that the lens 232 places onto the scintillator 231 during x-ray imaging can be removed or normalized by performing a gain correction, which is a common technique used in digital radiography. According to this aspect, the x-ray imaging device further includes at least one optical fiber 23 for conveying light from a proximal end (not shown) of the borescope 20 to an imaging end 120 thereof for illuminating the test object (not shown) during visible imaging.

According to a thirteenth aspect, the box 140 includes an opening 151 through which the optical fiber 23 extends. The opening is sized and configured to snuggly fit around the optical fiber. An exemplary fiber includes a light source end 152, as illustrated in FIGS. 5 and 6 for illuminating the test object during visual imaging. For example, the light source end extends less than about 2.5 cm outside the box. According to a fourteenth aspect, the x-ray imaging device 200 further includes means for articulating the optical fiber. The articulation means (not shown) preferably extend through the borescope 20.

According to another aspect, the fiber optic scintillator 231 has an antireflective coating (not shown) on the input surface 234 thereof. According to this aspect, the lens has an antireflective coating (not shown), at least on the side of the lens facing the fiber optic scintillator. The antireflective coatings on the lens and on the fiber optic scintillator reduce undesirable back reflections between the fiber optic scintillator and the lens during both x-ray and visual imaging.

Advantageously, the x-ray imaging device 200 according to the fourth embodiment aligns visible and x-ray imaging using a fixed x-ray detector 231 and imager 132, eliminating the need for slidable mountings.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An x-ray imaging device comprising:
   a borescope; and
   an x-ray detector positioned at a distal end of said borescope, wherein said x-ray detector is configured to be movable into an optical path and out of the optical path.

2. The x-ray imaging device of claim 1, further comprising:
   an optical path changer for changing an optical path of light emitted from said x-ray detector, said optical path changer being positioned between said x-ray detector and the distal end of said borescope.

3. The x-ray imaging device of claim 2, wherein said optical path changer includes a mirror.

4. The x-ray imaging device of claim 1, wherein said x-ray detector is constrained to move along a sliding axis.

5. The x-ray imaging device of claim 1, further comprising:
   an auxiliary optical system positioned between said x-ray detector and the distal end of said borescope and traveling with said x-ray detector into and out of the optical path.

6. The x-ray imaging device of claim 5, wherein said auxiliary optical system includes an auxiliary lens.

7. The x-ray imaging device of claim 1, further comprising:
   a primary optical system positioned between said x-ray detector and the distal end of said borescope.

8. The x-ray imaging device of claim 7, wherein said primary optical system includes a primary lens.

9. The x-ray imaging device of claim 1, wherein said x-ray detector includes a scintillation screen.

10. The x-ray imaging device of claim 9, wherein said scintillation screen comprises cesium iodide.

11. The x-ray imaging device of claim 9, wherein said scintillation screen is opaque to visible light incident on an incident edge of said scintillation screen.

12. The x-ray imaging device of claim 11, wherein said scintillation screen includes:
    a coating formed on the incident edge of said scintillation screen, said coating being opaque to visible light.

13. The x-ray imaging device of claim 1, wherein said borescope includes a waveguide for guiding electromagnetic radiation from the distal end to a proximal end of said borescope.

14. The x-ray imaging device of claim 13, wherein said waveguide includes a coherent fiber optic bundle.

15. The x-ray imaging device of claim 13, further comprising:
    an imager for converting the electromagnetic radiation to an electronic format, said imager being positioned at the proximal end of said borescope.

16. The x-ray imaging device of claim 15, wherein said imager comprises a photosensor array.

17. The x-ray imaging device of claim 1, further comprising:
    an imager for converting an image to an electronic signal, said imager being positioned between the distal end of said borescope and said x-ray detector.

18. The x-ray imaging device of claim 17, wherein said imager comprises a photosensor array.

19. The x-ray imaging device of claim 13, wherein said borescope further includes a second waveguide for guiding light from the proximal end to the distal end of said borescope for illuminating a surface during visual imaging.

20. The x-ray imaging device of claim 19, wherein said second waveguide includes at least one optical fiber.

21. An x-ray imaging device comprising:
    a borescope;
    a box extending over an imaging end of said borescope, said box including an aperture;
    an x-ray imager mounted in said box; and
    an optical path changer mounted in said box, wherein said x-ray imager and said optical path changer are slidably mounted in said box for sliding between a visible imaging position and an x-ray imaging position, and wherein said optical path changer is aligned with the aperture of said box in the visual imaging position, and said x-ray imager is exposed to an x-ray source in the x-ray imaging position.

22. The x-ray imaging device of claim 21, wherein said box is formed of a material, which material is substantially opaque to visible light and is substantially transparent to x-rays.

23. The x-ray imaging device of claim 22, wherein said optical path changer is mounted at a rear edge of said x-ray imager.

24. The x-ray imaging device of claim 23, wherein said optical path changer includes a prism having a reflective front face.

25. The x-ray imaging device of claim 22, wherein said x-ray imager includes:
    an x-ray detector which converts an x-ray flux to a spatial intensity pattern of light; and
    an imager which converts the spatial intensity pattern of light to an electronic signal,
    wherein said x-ray imaging device further comprises a conductive path for relaying the electronic signal from said imager to a proximal end of said borescope.

26. The x-ray imaging device of claim 25, wherein said x-ray detector includes a scintillator screen which is bonded to said imager.

27. The x-ray imaging device of claim 25, wherein said imager includes a photosensor array.

28. The x-ray imaging device of claim 25, wherein said x-ray imager further includes an optically transparent interface, said x-ray detector being bonded to said imager at said optically transparent interface.

29. The x-ray imaging device of claim 22, wherein said x-ray imager includes an x-ray detector, said x-ray detector comprising a photoconductor.

30. The x-ray imaging device of claim 29, wherein said x-ray imager includes a read-out structure, said read-out structure being electrically connected to said photoconductor.

31. The x-ray imaging device of claim 22, further comprising a primary optical system positioned between said optical path changer and a distal end of said borescope.

32. The x-ray imaging device of claim 31, wherein said primary optical system includes a lens.

33. The x-ray imaging device of claim 22, further comprising:
   a visible imager positioned at a proximal end of said borescope, said visible imager for converting an image to an electronic signal,
   wherein said borescope further includes a coherent waveguide for conveying the image at a distal end to the proximal end of said borescope.

34. The x-ray imaging device of claim 33, wherein said coherent waveguide includes a coherent fiber optic bundle.

35. The x-ray imaging device of claim 33, wherein said visible imager comprises a photosensor array.

36. The x-ray imaging device of claim 22, further comprising:
   a visible imager positioned at a distal end of said borescope, said visible imager for converting an image to an electronic signal,
   wherein said borescope further includes a conductive path for relaying the electronic signal from said visible imager to a proximal end of said borescope.

37. The x-ray imaging device of claim 36, wherein said visible imager comprises a photosensor array.

38. The x-ray imaging device of claim 23, further comprising a shutter positioned on said aperture, wherein said shutter is open during visible imaging and shut during x-ray imaging.

39. An x-ray imaging device comprising:
   a borescope;
   a box extending over an imaging end of said borescope, said box including an aperture, and said box being formed of a material which is substantially opaque to visible light;
   an x-ray detector mounted in said box;
   an imager mounted in said box;
   a conductive path for conveying an electronic signal from said imager to a proximal end of said borescope; and
   a shutter positioned in the aperture, wherein said shutter is configured to be open during visible imaging and closed during x-ray imaging.

40. The x-ray imaging device of claim 39, wherein said shutter is substantially coextensive with said x-ray detector, is substantially opaque to visible light, and possesses an x-ray absorptivity less than about twenty percent.

41. The x-ray imaging device of claim 39, wherein the material and said shutter possess an x-ray absorptivity less than about twenty percent.

42. The x-ray imaging device of claim 39, wherein said x-ray detector comprises a fiber optic scintillator.

43. The x-ray imaging device of claim 42, wherein said imager comprises a photosensor array that is in optical contact with said x-ray detector.

44. The x-ray imaging device of claim 43, further comprising:
   an optical system for focusing light onto an input surface of said fiber optic scintillator; and
   at least one optical fiber that extends through said borescope to convey light from the proximal end of said borescope to a distal end of said borescope for illumination of a test object during visible imaging.

45. The x-ray imaging device of claim 44, wherein said optical system comprises a lens possessing an x-ray absorptivity less than about twenty percent.

* * * * *